(12) United States Patent
Coroneo

(10) Patent No.: US 11,090,152 B2
(45) Date of Patent: *Aug. 17, 2021

(54) LENS DESIGN

(71) Applicant: Minas Theodore Coroneo, Vaucluse (AU)

(72) Inventor: Minas Theodore Coroneo, Vaucluse (AU)

( * ) Notice: Subject to any disclaimer, the term of this patent is extended or adjusted under 35 U.S.C. 154(b) by 33 days.

This patent is subject to a terminal disclaimer.

(21) Appl. No.: 16/504,914

(22) Filed: Jul. 8, 2019

(65) Prior Publication Data

US 2019/0336275 A1   Nov. 7, 2019

Related U.S. Application Data

(63) Continuation of application No. 15/519,486, filed as application No. PCT/AU2015/050634 on Oct. 15, 2015, now Pat. No. 10,383,722.

(60) Provisional application No. 62/064,262, filed on Oct. 15, 2014.

(51) Int. Cl.
| | | |
|---|---|---|
| *A61F 2/16* | (2006.01) | |
| *G02C 7/04* | (2006.01) | |
| *A61B 3/12* | (2006.01) | |
| *G02B 1/04* | (2006.01) | |
| *G02C 7/14* | (2006.01) | |
| *A61F 2/14* | (2006.01) | |

(52) U.S. Cl.
CPC .............. *A61F 2/1656* (2013.01); *A61B 3/12* (2013.01); *A61F 2/1648* (2013.01); *G02B 1/041* (2013.01); *G02C 7/04* (2013.01); *G02C 7/14* (2013.01); *A61F 2/1451* (2015.04); *A61F 2002/1696* (2015.04); *A61F 2002/16902* (2015.04)

(58) Field of Classification Search
CPC ............ A61F 2/1656; A61F 2002/1696; A61F 2002/16902
See application file for complete search history.

(56) References Cited

U.S. PATENT DOCUMENTS

| | | |
|---|---|---|
| 4,596,578 A | 6/1986 | Kelman |
| 4,673,406 A | 6/1987 | Schlegel |
| 5,728,156 A | 3/1998 | Gupta |
| 6,468,306 B1 | 10/2002 | Paul |

(Continued)

FOREIGN PATENT DOCUMENTS

| | | |
|---|---|---|
| EP | 2 319 457 A1 | 5/2011 |
| WO | WO 2014/005074 A1 | 1/2014 |

OTHER PUBLICATIONS

Coroneo, et al. 2003 "Off-axis edge glare in pseudophakic dyspotopsia" *Journal of Cataract & Refractive Surgery* 29(10): 1969-1973.

(Continued)

*Primary Examiner* — Jerrah Edwards
*Assistant Examiner* — Javier G Blanco
(74) *Attorney, Agent, or Firm* — Knobbe, Martens, Olson & Bear, LLP

(57) ABSTRACT

An intraocular lens configured to reduce or eliminate oblique incident light photic disturbances in the eye, said lens comprising anterior and posterior surfaces defining a central lens optic extending from said anterior to said posterior surfaces and a peripheral portion outside of the central lens optic, wherein the peripheral portion is a prismatic lens which redirects oblique incident light on the peripheral portion forward of the nasal retina in the eye and onto the ciliary body/pars plana region.

20 Claims, 3 Drawing Sheets

(56) References Cited

U.S. PATENT DOCUMENTS

| | | |
|---|---|---|
| 6,835,204 B1 | 12/2004 | Stork |
| 7,217,289 B2 | 5/2007 | Coroneo |
| 2003/0144733 A1 | 7/2003 | Brady et al. |
| 2008/0027537 A1 | 1/2008 | Gerlach |
| 2008/0269882 A1 | 10/2008 | Simpson |
| 2008/0269885 A1 | 10/2008 | Simpson |
| 2008/0269886 A1 | 10/2008 | Simpson |
| 2008/0269889 A1 | 10/2008 | Simpson |
| 2008/0269890 A1 | 10/2008 | Simpson |
| 2008/0269891 A1 | 10/2008 | Simpson |
| 2009/0088842 A1 | 4/2009 | Morgan |
| 2011/0054603 A1 | 3/2011 | Morgan |
| 2014/0180408 A1 | 6/2014 | Angelopoulos et al. |

OTHER PUBLICATIONS

Extended European Search Report in corresponding European Patent Application No. 15850552.9, dated May 7, 2018.

LENS DESIGN

TECHNICAL FIELD

The present invention generally relates to ocular lens and in particular to intraocular lenses, artificial corneas and contact lenses which alleviate or eliminate photic disturbances in the eye.

BACKGROUND

Certain eye conditions can be treated with ocular lenses which adjust the optical properties of the eye. Such lenses include contact lenses, artificial corneas and intraocular lenses.

In the example of intraocular lenses, the normal crystalline lens of an eye is replaced with an intraocular lens formed of materials such as polymethyl methacrylate, virgin silicone or acrylic based materials, which are generally soft and flexible to allow the lens to be folded for insertion via a small incision in the eye.

Patients fitted with ocular lenses often report visual disturbances including glare, streaks and/or shadows in the temporal visual field. These visual disturbances are termed photic disturbances. In the pseudophakic human eye in particular (where the crystalline lens has been surgically removed and replaced) photic disturbances (in this case termed pseudophakic dysphotopsia) can adversely affect the quality of vision of a high proportion of patients implanted with an intraocular lens.

Where secondary images are formed in the temporal visual field, the photic disturbances are termed positive dysphotopsia. Where shadows are formed in the temporal visual field, the photic disturbances are termed negative dysphotopsia. In pseudophakic patients the temporal field of vision can be constricted.

It has been shown that reflected rays of oblique light can cause phototic disturbances, as outlined in U.S. Pat. No. 7,217,289, the disclosure of which is incorporated herein by reference.

Such photic disturbances are common as greater than 50% of light striking the anterior eye is scattered, with a portion of the reflected light falling incident on the eye at oblique angles. Furthermore, the lens of the eye (natural crystalline or intraocular lens) is subject to peripheral light focusing over a broad range of angles, for example, up to 30°. The reason that positive dysphotopsia is noticeable is that the arcs of light that are focused on the nasal retina are 3.7 to 4.8 times more intense than incident light and so are perceived as brighter than the background illumination.

Negative dysphotopsia (temporal darkness) occurs when light is shunted away from the peripheral retina by the prismatic effect of many modern intraocular lenses. This phenomenon can also result in a reduction of the peripheral field in the order of 20%, reduces quality of vision, and hinders the ability of ophthalmologists to clinically view the peripheral retina by ophthalmoscopy.

The present invention seeks to provide an improved design for ocular and intraocular lenses which is believed to alleviate or eliminate photic disturbances, improve field of vision and/or visualisation of the peripheral retina. The present invention further seeks to improve the ability of ophthalmologists to clinically view the peripheral retina by ophthalmoscopy.

The reference in this specification to any prior publication (or information derived from it), or to any matter which is known, is not, and should not be taken as, an acknowledgement or admission or any form of suggestion that prior publication (or information derived from it) or known matter forms part of the common general knowledge in the field of endeavour to which this specification relates.

BRIEF SUMMARY

According to a first aspect, the present invention provides an intraocular lens configured to reduce or eliminate oblique incident light photic disturbances in the eye, said lens comprising anterior and posterior surfaces defining a central lens optic extending from said anterior to said posterior surfaces and a peripheral portion outside of the central lens optic, wherein the peripheral portion is a prismatic lens optic which redirects oblique incident light on the peripheral portion forward of the nasal retina in the eye and onto the light-insensitive ciliary body/pars plana.

According to another aspect, the present invention provides an intraocular lens including:

a central lens optic with an anterior surface and a posterior surface; and, a peripheral portion with an anterior surface and a posterior surface, wherein the peripheral portion is adjacent to the central lens optic and wherein the peripheral portion is a prismatic lens, and wherein the prismatic lens redirects oblique incident light onto an internal portion of the eye without light receptors.

According to an additional aspect, the present invention provides an intraocular lens wherein the central lens optic is in the form of a disc and the prismatic lens is disposed concentrically around the perimeter of the central lens optic such that a proximal portion of the prismatic lens is adjacent to the central lens optic and a distal portion of the prismatic lens optic is remote from the central lens optic.

According to an additional aspect, the present invention provides an intraocular lens wherein the diameter of the intraocular lens is between about 5 mm to 7 mm.

According to an additional aspect, the present invention provides an intraocular lens wherein the diameter of the intraocular lens is about 6 mm.

According to an additional aspect, the present invention provides an intraocular lens wherein the diameter of the central lens optic is between about 2 mm to 4 mm.

According to an additional aspect, the present invention provides an intraocular lens wherein the diameter of the central lens optic is about 3 mm.

According to an additional aspect, the present invention provides an intraocular lens wherein the distance between the proximal and distal portions of the prismatic lens along a line normal to the tangent of the central lens optic is between about 1 mm to 2 mm.

According to an additional aspect, the present invention provides an intraocular lens wherein the distance between the proximal and distal portions of the prismatic lens along a line normal to the tangent of the central lens optic is about 1.5 mm.

According to an additional aspect, the present invention provides an intraocular lens wherein the prismatic lens is a triangular prism.

According to an additional aspect, the present invention provides an intraocular lens wherein the thickness of the prismatic lens at its junction with the central lens optic is about 0.1 mm.

According to an additional aspect, the present invention provides an intraocular lens wherein the thickness of the distal portion of the prismatic lens is between about 0.65 mm to 1 mm.

According to an additional aspect, the present invention provides an intraocular lens wherein the thickness of the distal portion of the prismatic lens is about 0.79 mm.

According to an additional aspect, the present invention provides an intraocular lens wherein the angle between the anterior and posterior surface of the triangular prism is between about 20° to 30°.

According to an additional aspect, the present invention provides an intraocular lens wherein the angle between the anterior and posterior surface of the triangular prism is about 25°.

According to an additional aspect, the present invention provides an intraocular lens wherein the power of the prismatic lens is between about 1 D to 100 D.

According to an additional aspect, the present invention provides an intraocular lens wherein the power of the prismatic lens is between about 5 D to 35 D.

According to an additional aspect, the present invention provides an intraocular lens wherein the power of the prismatic lens is 20 D.

According to an additional aspect, the present invention provides an intraocular lens wherein the radius of curvature of the anterior surface of the central lens optic is between about R5.00 to R15.00.

According to an additional aspect, the present invention provides an intraocular lens wherein the radius of curvature of the anterior surface of the central lens optic is R9.72.

According to an additional aspect, the present invention provides an intraocular lens wherein the radius of curvature of the posterior surface of the central lens optic is between about R20.00 to R50.00.

According to an additional aspect, the present invention provides an intraocular lens wherein the radius of curvature of the posterior surface of the central lens optic is R35.00.

According to an additional aspect, the present invention provides an intraocular lens is formed of a single continuous material.

According to an additional aspect, the present invention provides an intraocular lens formed from a polymeric material.

According to an additional aspect of the present invention, the polymeric material is a hydrogel or silicone.

According to an additional aspect of the present invention, the polymeric material is polymethyl methacrylate, virgin silicone or an acrylic based material.

According to an additional aspect of the present invention, oblique incident light is incident upon the temporal limbus of the eye at an angle of about 65° to 91°.

According to an additional aspect, the present invention provides an intraocular lens wherein the central lens optic is visually transparent.

According to an additional aspect, the present invention provides an intraocular lens wherein the peripheral portion is visually transparent.

According to an additional aspect, the present invention provides an intraocular lens wherein the intraocular lens is restorably deformable.

According to an additional aspect, the present invention provides an intraocular lens wherein the intraocular lens is for the treatment of a cataract.

According to an additional aspect, the present invention provides an intraocular lens wherein the intraocular lens is a phakic intraocular lens for the treatment of refractive error.

In an additional aspect, the present invention provides an intraocular lens includes one or more haptics extending from the peripheral portion for securing the intraocular lens to the eye.

According to another aspect the present invention provides a use of the intraocular lens as herein described for alleviating photic disturbances including positive dysphotopsia and negative dysphotopsia.

According to another aspect the present invention provides a use of the intraocular lens as herein described to view the peripheral retina by ophthalmoscopy.

BRIEF DESCRIPTION OF FIGURES

Example embodiments should become apparent from the following description, which is given by way of example only, of at least one preferred but non-limiting embodiment, described in connection with the accompanying figures.

Figure 1:
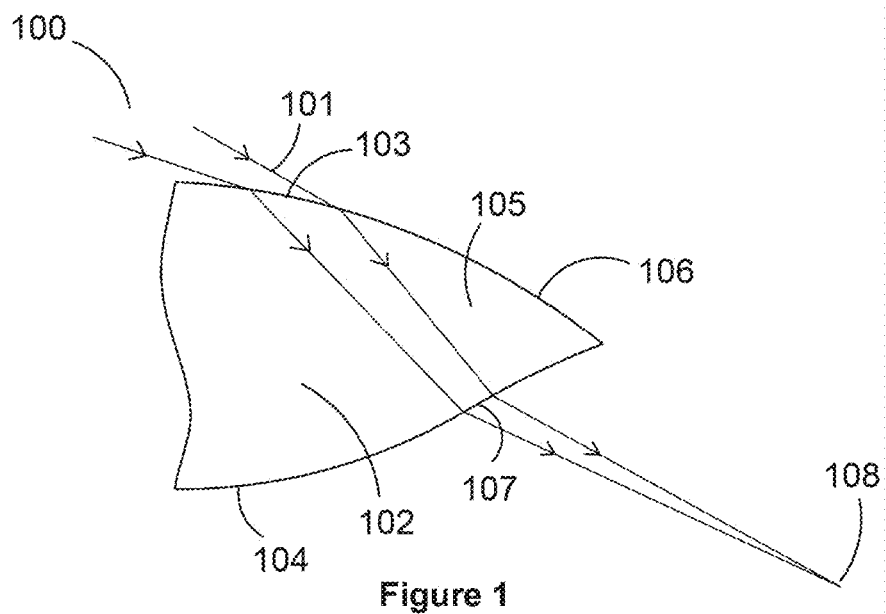
FIG. 1 illustrates the optical effect of the nasal perimeter of a prior art intraocular lens on obliques incident light.

PARTS LIST 100 prior art intraocular lens
101 oblique rays
102 main portion of intraocular lens
103 anterior surface of main portion
104 posterior surface of main portion
105 peripheral portion of intraocular lens
106 anterior surface of peripheral portion
107 posterior surface of peripheral portion
108 foci of oblique rays
200 intraocular lens of present invention
202 main portion of intraocular lens
203 anterior surface of main portion
204 posterior surface of main portion
205 peripheral portion of intraocular lens
206 anterior surface of peripheral portion
207 posterior surface of peripheral portion
208 foci of oblique rays
209 central lens optic
210 haptics
211 prismatic lens
212 proximal portion of prismatic lens
213 distal portion of prismatic lens
214 first junction region
215 second junction region

PREFERRED EMBODIMENTS

The following modes, given by way of example only, are described in order to provide a more precise understanding of the subject matter of a preferred embodiment or embodiments.

In the figures, incorporated to illustrate features of an example embodiment, like reference numerals are used to identify like parts throughout the figures.

Referring to FIG. 1, shown is a schematic of a prior art intraocular lens 100. Intraocular lenses 100 are generally formed from polymeric materials such as hydrogels and silicones. Intraocular lenses are also generally configured to be restorably deformable such that the lens can be folded to a reduced size for insertion into the eye through a small incision.

FIG. 1 shows the portion of an intraocular lens 100 nearest to the nasal retina when the lens is inserted into the eye. This portion may be referred to as the nasal perimeter of the intraocular lens. Oblique rays 101 originating from a temporal field fall incident on the anterior surface 103 of the main portion 102 of the intraocular lens 100. The oblique off-axis light is typically incident on the temporal limbus of the eye at an angle of about 65° to 91°. The oblique rays 101 are refracted at the anterior surface 103 of the main portion 102 and propagate through the intraocular lens 100, falling incident on the posterior surface of the peripheral portion 107. At the posterior surface 107, the oblique rays 101 are refracted again, with the refracted oblique rays converging on a focus 108. The oblique rays 101 refracted by the posterior surface of the intraocular lens 107 are refracted posteriorly in relation to the oblique rays 101 incident on the anterior surface 103. Thereby, the foci 108 for oblique rays occurs in the nasal interior of the eye, including the nasal retina, thus causing photic disturbances such as unwanted image formation characteristic of positive dysphotopsia.

The nasal perimeter of the intraocular lens 100 shunts light towards the optical axis of said lens. Thus, whilst the focus 108 of oblique rays 101 occur in the nasal interior of the eye leading to positive dysphotopsia, a region may exist between this focus 108 and the light insensitive ciliary body/pars plana of the eye. This region is deprived of light by the characteristics of the intraocular lens 100, and is perceived as the temporal darkness of negative dysphotopsia. This area of retina is difficult to visualise by ophthalmoscopy and consequently, pathology in this area of the retina would be difficult to detect.

Figure 2:
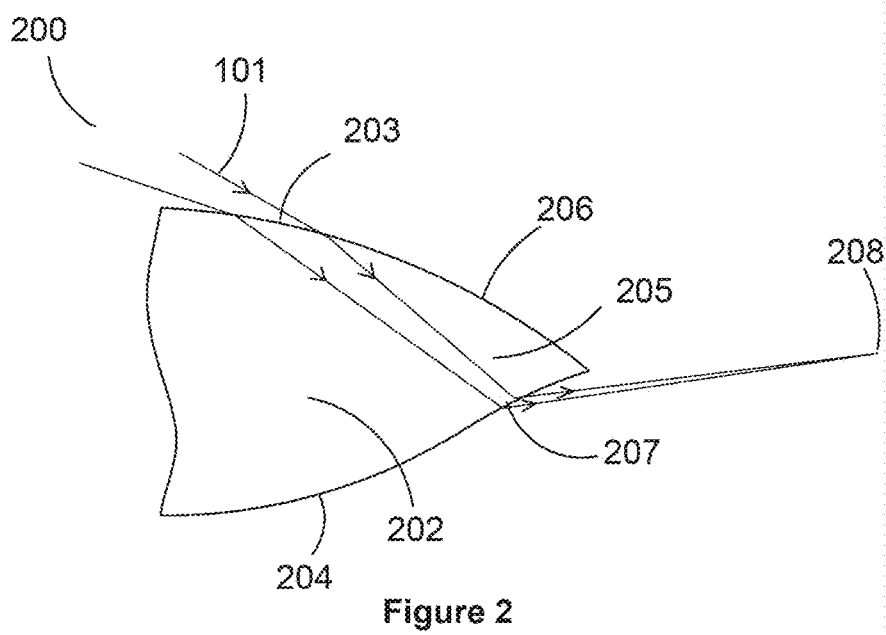
FIG. 2 illustrates the optical effect of the of the nasal perimeter of a intraocular lens according to the present invention, as applied to oblique incident.

Referring to FIG. 2, shown is a schematic of an intraocular lens 200 according to the present invention. It will be noted that this schematic describes the effect on oblique rays 101 incident on the intraocular lens 200, rather than describe the particular physical structure of the lens.

FIG. 2 also depicts the nasal perimeter of the intraocular lens 200 including a main portion 202 distal to the nasal retina and peripheral portion 205 proximal to the nasal retina. Anterior and posterior surfaces are also shown for both the main portion and the peripheral portion.

The peripheral portion 205 is configured with prismatic properties which cause the oblique rays 101 to refract anteriorly or laterally at the posterior surface 207 in relation to the oblique rays incident on the anterior surface 203 of the intraocular lens 200. Otherwise stated, the peripheral portion is configured to shunt light away from the optical axis, in contrast to the peripheral portion of the prior art lens 100. This effect adjusts the foci 208 anteriorly when compared with the foci 108 of FIG. 1. Consequently, the prismatic peripheral portion 205 can move the foci 108 away from the nasal retina and onto the ciliary body/pars plana of the eye, which are insensitive to light. This effect can overcome or alleviate photic disturbances caused by oblique rays. Furthermore, by adjusting the foci 108 of oblique rays 101 onto the ciliary body/pars plana, the entire retina is able to receive light from the intraocular lens 200, thus avoiding the temporal darkness associated with negative dysphotopsia.

Figure 3:
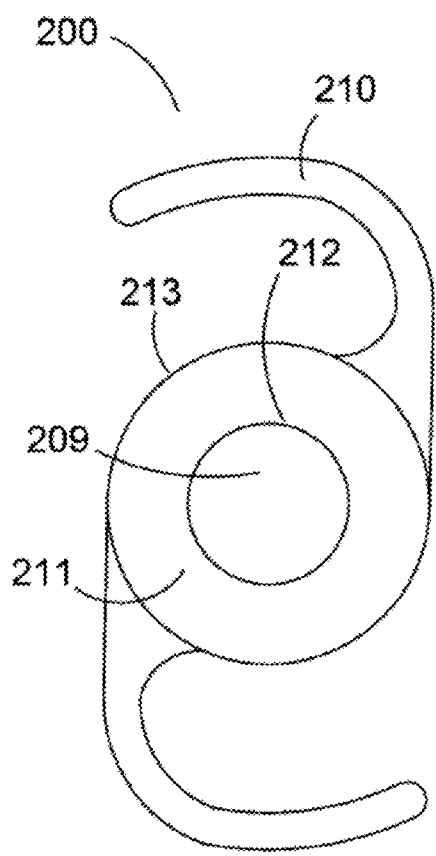
FIG. 3 illustrates a plan view of an intraocular lens according to the present invention.

FIG. 3 shows an embodiment of an intraocular lens 200 according to the present invention in plan view. In the centre of the lens is a central lens optic 209, which is generally analogous to the main portion 202 of the embodiment of FIG. 2. Located at or adjacent to the periphery of the central lens optic 209 is a prismatic lens 211, which corresponds generally to the peripheral portion 205 of the embodiment of FIG. 2.

The central lens optic 209 is generally shaped to obtain the desired optical correction required by the wearer of the lens. The central lens portion may be generally disk or plate like in shape, and formed from a single continuous material.

The prismatic lens 211 may be disposed concentrically to the central lens optic 209 at or adjacent to the perimeter of the central lens optic 209. The central lens optic 209 may be separated by a first junction region 214 such that the prismatic lens 211 is substantially discreet from the central lens optic 209. However, the first junction 214 need not be a separate portion of the intraocular lens 200 to the central lens optic 209 or the prismatic lens 211; it may describe a general region therebetween. The first junction 214 may be small portion of the intraocular lens 200 where the intraocular lens 200 is thinnest.

At the portion of the prismatic lens 211 distal to the central lens optic 209 are haptics 210, which are used to attach to an internal portion of the eye to hold the intraocular lens in place. The haptics 210 may also be continuous, that is, formed from the same material as the peripheral portion from which they extend. Alternatively the haptics 210 can be formed from a separate material to the peripheral 205 portion and attached thereto. The haptics 210 may be separated from the prismatic lens by a second junction region 215 such that the haptics are substantially discreet from the prismatic lens.

It will be appreciated that many forms of haptics 210 are known to a person skilled in the art as suitable for use with a intraocular lens. Although the figures depict an angular form, other forms such as plates fall within the scope of the invention.

Figure 4:
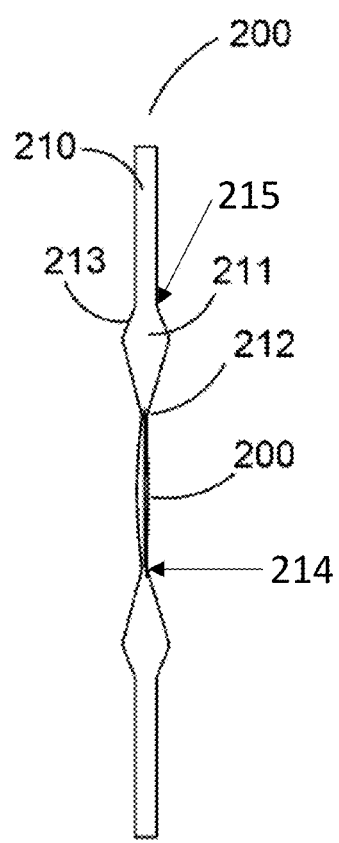
FIG. 4 illustrates a side view of an intraocular lens according to the present invention.

FIG. 4 offers a side view of the intraocular lens 200 of FIG. 3. In the embodiment of FIG. 4, the prismatic lens 211 is configured as a triangular prism with a thinnest part at the proximal portion 212 and a thickest part at the distal portion 213. The proximal portion of the prismatic lens 211 may converge with central lens optic 209 at the first junction region 214, which may be the thinnest part of the intraocular lens overall. The triangular prism of the shown embodiment is also arranged symmetrically between the anterior and posterior portion of the intraocular lens. However, it is to be appreciated that other prismatic lenses are capable of performing the present invention, including lenses that effectively acts as triangular prisms.

Surprisingly, it was found that when a prismatic lens 211 was formed at the location at the perimeter of the central lens optic 209, or immediately adjacent the perimeter at the central lens optic 209, there was no interference observed with the vision in the forward focusing direction. In addition it was also surprisingly found that the field of vision was increased.

Figure 5:
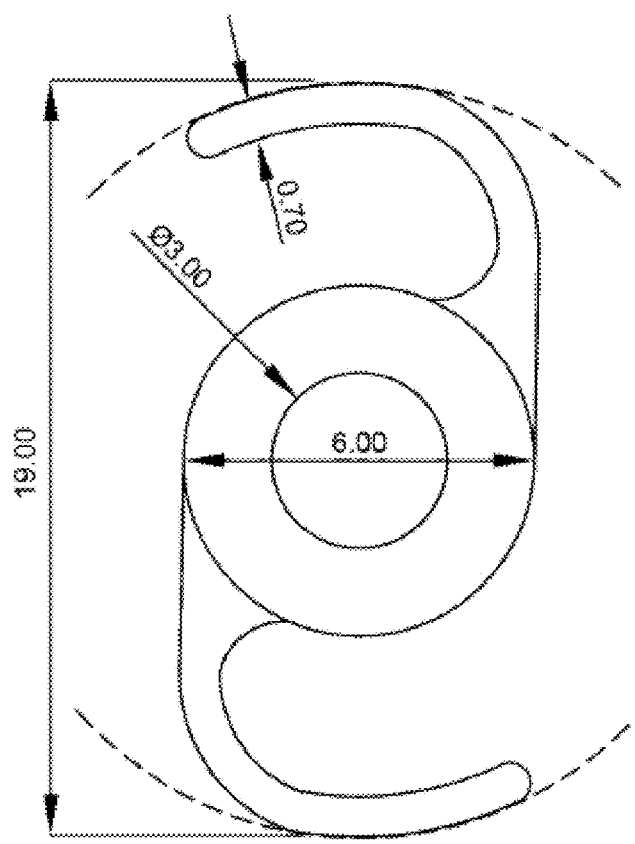
FIG. 5 illustrates a plan view of an intraocular lens according to the present invention with indicative dimensions.
Figure 6:
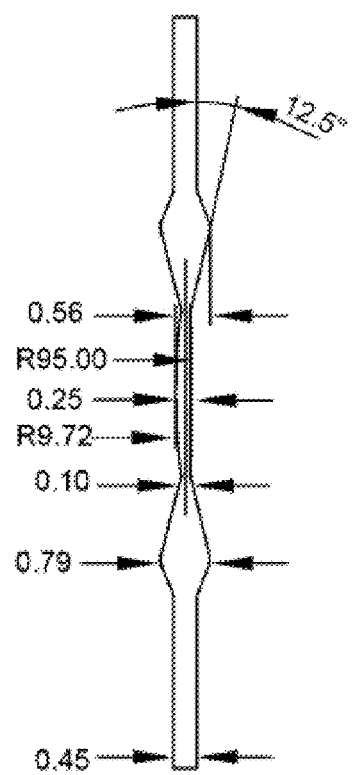
FIG. 6 illustrates a side view of an intraocular lens according to the present invention with indicative dimensions.

By way of example, FIG. 5 is an example embodiment of FIG. 3 with some indicative dimensions shown. Similarly, FIG. 6 gives some indicative dimensions for the embodiment of FIG. 4. In these example embodiments, the diameter of the central lens optic 209 is about 3 mm and the diameter of the annual prismatic lens 211 disposed around the central lens optic 209 is about 6 mm. The thickest part of the central lens optic 209 is about 0.25 mm and occurs at the centre of the central lens optic 209. The thickness of the central lens optic reduces to about 0.1 mm at the outside perimeter of the central lens optic. This thinnest region may be considered the first junction region 214 and as such, may also be considered the thinnest region of the prismatic lens 211, which occurs at the proximal region 212. The thickness of the prismatic lens 211 increases from the proximal region towards the distal region where the prismatic lens is at its thickest at about 0.79 mm. The radius of curvature of the anterior surface of the central lens optic 209 is about R9.72 whereas the radius of curvature of the posterior surface of the central lens optic is about R95. The prismatic lens 211 is configured as an isosceles triangle symmetrically arranged about an axis of the central lens optic with a vertex angle formed between the anterior and posterior surfaces of 25°. It is to be appreciated that these dimensions are indicative only, and different dimensions may be required due to the desired optical correction required and the specific anatomy of the eye to which the intraocular lens is to be implanted.

Although the preceding embodiments are applied to intraocular lenses, it is to be understood that the invention equally applies to other lenses such as artificial corneas or contact lenses. The invention also applies to phakic intraocular lens for the treatment of refractive error.

The present invention can be configured such that the foci 108 of oblique rays 101 occurs on the ciliary body/pars plana of the eye. This avoids the formation of a region around the nasal retina that would otherwise be deprived of light. This result allows a medical practitioner to clinically view the peripheral retina by ophthalmoscopy. It is important that eye care professionals are able to view the peripheral retina, usually by the technique of ophthalmoscopy. This is because certain conditions preferentially afflict this area, including retinal holes or tears that forebode retinal detachment, the risk of which increases after cataract surgery. To date, visualisation of the peripheral retina is difficult in patients in whom intraocular lenses 100 have been implanted. It has been presumed that this is because of the phenomenon of opacification of the lens capsule into which intraocular lenses 100 are implanted and which surround the intraocular lens. In reality when the ophthalmoscope light is shone into the eye, it is shunted posteriorly by the prismatic effect of the prior art intraocular lens optics, away from the peripheral retina, making visualisation virtually impossible. Furthermore, to treat retinal holes or tears, or other conditions such as diabetic retinopathy which can affect the peripheral retina, treatments which involve the use of lasers may be required. Again, this is difficult because laser light cannot be aimed directly at this part of the retina because of the intraocular lens prismatic light shunting effect. The intraocular lens here described will allow better viewing of the peripheral retina as compared to conventional lenses as well as easier use of treatment modalities such as the use of lasers.

Many modifications will be apparent to those skilled in the art without departing from the scope of the present invention.

It is to be appreciated that those skilled in the art would appreciate that while the magnitude of prism in the peripheral portion is practically unlimited, different placements and amounts would result in different surface curvatures and thickness profiles which may require additional transition or blending regions between the central lens optic and the peripheral portion.

The invention claimed is:

1. An intraocular lens (IOL) configured to reduce or eliminate oblique incident light photic disturbances in the eye, said intraocular lens comprising:

a central lens optic with an anterior surface and a posterior surface, wherein the central lens optic is visually transparent;

a peripheral portion with an anterior surface and a posterior surface, wherein the peripheral portion is visually transparent; and one or more haptics radially extending from the peripheral portion for securing the intraocular lens to the eye, wherein the peripheral portion is a prismatic lens which redirects oblique incident light on the peripheral portion forward of the nasal retina in the eye and onto the ciliary body/pars plana region in the eye, wherein the central lens optic is in the form of a disc, wherein the prismatic lens is joined and disposed concentrically around the entire perimeter of the central lens optic such that a proximal portion of the prismatic lens is adjacent to the central lens optic and a distal portion of the prismatic lens is radially remote from the central lens optic, wherein a thickness of the prismatic lens is larger than a thickness of the central lens optic, wherein, in the sagittal plane, the prismatic lens is configured as a triangular prism with a thinnest part at the proximal portion and a thickest part at the distal portion.

2. The intraocular lens according to claim 1, wherein the diameter of the intraocular lens is between about 5 mm to 7 mm.

3. The intraocular lens according to claim 1, wherein the diameter of the intraocular lens is about 6 mm.

4. The intraocular lens according to claim 1, wherein the diameter of the central lens optic is between about 2 mm to 4 mm.

5. The intraocular lens according to claim 4, wherein the diameter of the central lens optic is about 3 mm.

6. The intraocular lens according to claim 1, wherein a thickness of the distal portion of the prismatic lens is between about 0.65 mm to 1 mm.

7. The intraocular lens according to claim 1, wherein a thickness of the distal portion of the prismatic lens is about 0.79 mm.

8. The intraocular lens according to claim 1, wherein an angle formed between the anterior and posterior surfaces of the triangular prism is between about 20° to 30°.

9. The intraocular lens according to claim 1, wherein an angle formed between the anterior and posterior surfaces of the triangular prism is about 25°.

10. The intraocular lens according to claim 1, wherein a power of the prismatic lens is between about 1 D to 100 D.

11. The intraocular lens according to claim 10, wherein the power of the prismatic lens is between about 5 D to 35 D.

12. The intraocular lens according to claim 11, wherein the power of the prismatic lens is 20 D.

13. The intraocular lens according to claim 1, wherein the intraocular lens is formed of a single continuous material.

14. The intraocular lens according to claim 1, wherein the intraocular lens is formed from a polymeric material.

15. The intraocular lens according to claim 14, wherein the polymeric material is a hydrogel or silicone.

16. The intraocular lens according to claim 14, wherein the polymeric material is polymethyl methacrylate, virgin silicone or an acrylic based material.

17. The intraocular lens according to claim 1, wherein the oblique incident light is incident upon the temporal limbus of the eye at an angle of about 65° to 91°.

18. The intraocular lens according to claim 1, wherein the intraocular lens is restorably deformable.

19. The intraocular lens according to claim 1, wherein the intraocular lens is for the treatment of a cataract.

20. The intraocular lens according to claim 1, wherein the intraocular lens is a phakic intraocular lens for the treatment of refractive error.

* * * * *